United States Patent
Lee et al.

(10) Patent No.: US 8,299,049 B2
(45) Date of Patent: Oct. 30, 2012

(54) **COMPOSITIONS COMPRISING AN EXTRACT OF *TIARELLA POLYPHYLLA* OR COMPOUNDS ISOLATED THEREFROM FOR PREVENTING AND TREATING CANCER DISEASES**

(75) Inventors: Hyeong-Kyu Lee, Daejeon (KR); Sei-Ryang Oh, Daejeon (KR); Kyungseop Ahn, Daejeon (KR); Joongku Lee, Daejeon (KR); Sangku Lee, Daejeon (KR); Ho-Jae Lee, Daejeon (KR); Doo-Young Kim, Daejeon (KR); Jung-Hee Kim, Daejeon (KR); Eun-Ah Kim, Naju-si (KR); Soon-Ja Choi, Daejeon (KR); Soo Hyun Kim, Seoul (KR); Jung Weon Lee, Seoul (KR); Su-Yong Choi, Sacheon-si (KR)

(73) Assignee: Korea Institute of Bioscience and Biotechnology (KR)

( * ) Notice: Subject to any disclaimer, the term of this patent is extended or adjusted under 35 U.S.C. 154(b) by 285 days.

(21) Appl. No.: 12/626,553

(22) Filed: Nov. 25, 2009

(65) Prior Publication Data
US 2010/0081638 A1    Apr. 1, 2010

Related U.S. Application Data

(63) Continuation of application No. PCT/KR2007/006169, filed on Nov. 30, 2007.

(30) Foreign Application Priority Data

May 26, 2007 (KR) .................. 10-2007-0051156

(51) Int. Cl.
*A61K 31/56* (2006.01)
(52) U.S. Cl. .................................................. 514/169
(58) Field of Classification Search .................. None
See application file for complete search history.

(56) References Cited

FOREIGN PATENT DOCUMENTS

| KR | 10-2001-0034867 A | 4/2001 |
| KR | 10-2003-0042123 A | 5/2003 |
| WO | 2007/004827 A | 1/2007 |
| WO | 2007/011148 A1 | 1/2007 |

OTHER PUBLICATIONS

Troiani et al.; "The use of xenograft models for the selection of cancer treatments with the EGFR as an example"; 2008; Clinical Reviews in Oncology/Hematology; 65: 200-211.*
Park et al.; 1999; Arch. Pharm. Res. 22(4): 428-431.*

(Continued)

*Primary Examiner* — Timothy Thomas
(74) *Attorney, Agent, or Firm* — Daniel J. Chalker; Edwin S. Flores; Chalker Flores, LLP

(57) ABSTRACT

The present invention relates to an anoikis-inducing agent comprising a *Tiarella polyphylla* extract, a tiarellic acid compound isolated therefrom or a pharmaceutically acceptable salt thereof, which is specific to cancer cells expressing a tumor-associated antigen L6 or a homolog thereof. The *Tiarella polyphylla* extract, the tiarellic acid compound isolated therefrom or pharmaceutically acceptable salt thereof of the present invention leads to loss of cell adhesion to reduce cancer cell proliferation and exhibits the effect of inducing cell death in cancer cells expressing a tumor-associated antigen L6 or a homolog thereof, thereby being used for preventing and treating cancer diseases due to a tumor-associated antigen L6 or a homolog thereof.

6 Claims, 17 Drawing Sheets

OTHER PUBLICATIONS

Ahn G S et al: "Triterpene compound having apoptosis induction effect", May 28, 2003, WPI / Thomson.

Moon H I et al: "The effect of tiarellic acid on the expressions of matrix metalloproteinase-1 and type 1 procollagen in ultraviolet irradiated cultured human skin fibroblasts", Journal of Ethnopharmacology, Elsevier Scientific Publishers Ltd, IE, vol. 98, No. 1-2, Apr. 8, 2005, pp. 185-189.

Zhang Xianwu, et al., Effect of Antineoplastic on Apoptosis, Inner Mongolia Medical Journal, 2006, 38(4), pp. 334-338.

European Search Report issued on Jun. 7, 2011 for European Application No. 07851172.2.

Moon, H.I. et al., Triterpenoid from *Tiarella polyphylla*, Regulation of type 1 procollagen and MMP-1 in ultraviolet irradiation of cultured old age human dermal fibroblasts, Arch. Pharm. Res. 2004, vol. 27, No. 10, pp. 1060-1064.

Park, S.H. et al., Anticomplement activities of oleanolic acid monodesmosides and bisdesmosides isolated from *Tiarella polyphylla*, Arch. Pharm. Res. 1999, vol. 22, No. 4, pp. 428-31.

Park, S.H. et al., Structure determination of a new lupane-type triterpene, tiarellic acid, isolated from *Tiarella polyphylla*, Arch. Pharm. Res. 2002, vol. 25, No. 1, pp. 57-60.

International Search Report from PCT/KR2007/006169.

Lee, Sin-Ae et al., Tetraspanin TM4SF5 mediates loss of contact inhibition through epithelial-mesenchymal transition in human hepatocarcinoma, The Journal of Clinical Investigation, Apr. 2008, vol. 118, Issue 4, pp. 1354-1366.

Lee, Sin-Ae, et al., "Tetraspanin TM4SF5 mediates loss of contact inhibition through epithelial-mesenchymal transition in human hepatocarcinoma." The Journal of Clinical Investigation, (2008) 118:4, 1354-1366.

Muller-Pillasch, F., et al., "Identification of a new tumour-associated antigen TM4SF5 and its expression in human cancer." Gene, an International Journal on Genes and Genomes, (1998), 25-30.

Pascual-LeTallec, Laurent, et al., "Identification of genes associated with the Corticotroph Phenotype in Bronchial Carcinoid Tumors." J Clin Endocrinol Metab, (2002), 87:11, 5015-5022.

Wright, Mark D., et al., "The L6 membrane proteins—a new four-transmembrane superfamily." Protein Science (2000), 9, 1594-1600.

* cited by examiner

US 8,299,049 B2

COMPOSITIONS COMPRISING AN EXTRACT OF *TIARELLA POLYPHYLLA* OR COMPOUNDS ISOLATED THEREFROM FOR PREVENTING AND TREATING CANCER DISEASES

CROSS-REFERENCE TO RELATED APPLICATIONS

This application is a continuation application under 35 U.S.C. §365(c) of International Application No. PCT/KR2007/006169, filed Nov. 30, 2007 designating the United States. International Application No. PCT/KR2007/006169 was published in English as WO2008/147005 A1 on Dec. 4, 2008. This application further claims the benefit of the earlier filing date under 35 U.S.C. §365(b) of Korean Patent Application No. 10-2007-0051156 filed May 26, 2006. This application incorporates herein by reference the International Application No. PCT/KR2007/006169 including the International Publication No. WO2008/147005 A1 and the Korean Patent Application No. 10-2007-0051156 in their entirety.

TECHNICAL FIELD

The present invention relates to a cancer cell-specific anoikis-inducing agent, comprising a *Tiarella polyphylla* extract, a tiarellic acid compound isolated therefrom or a pharmaceutically acceptable salt thereof, and to an anticancer composition or functional health food comprising the same.

BACKGROUND ART

Interaction between integrin and extracellular matrix (ECM) mediates cell adhesion, and integrin-mediated cell adhesion regulates the activities and localizations of diverse signaling molecules, and consequently cell functions or behaviors (Thiery, J. P. Epithelial-mesenchymal transitions in tumour progression. Nat Rev Cancer, 2, pp. 442-54, 2002; Brakebusch, C. and Fassler, R., The integrin-actin connection, an eternal love affair, EMBO J, 22, pp. 2324-33, 2003). When integrins interact extracellularly to extracellular matrix (ECM) at focal adhesions, intracellular cytoplasmic tails of integrin subunits recruit diverse focal adhesion molecules, including adaptor proteins such as paxillin and p130Cas, and signaling molecules such as focal adhesion kinase (FAK) and c-Src (DeMali, K. A. et al., K. Integrin signaling to the actin cytoskeleton, Curr Opin Cell Biol., 15, pp. 572-82, 2003; Carragher, N. O. and Frame, M. C., Focal adhesion and actin dynamics: a place where kinases and proteases meet to promote invasion, Trends Cell Biol, 14, pp. 241-9, 2004). The recruitment of intracellular signaling molecules results in their activation, leading to reorganization of the actin cytoskeleton, and subsequently to changes in cell shape (Juliano, R. L. et al., Integrin regulation of cell signaling and motility, Biochem Soc Trans, 32, pp. 443-6, 2004). Since the integrins at the focal adhesions are linked to actin filaments through protein complexes (at their cytoplasmic tails), inefficient assembly of focal adhesion molecules or abnormal reorganization of actin filaments can cause cells to be round-shaped with concomitant loss of focal adhesions, leading to consequent detachment of cells from basement membrane (Hirohashi, S. and Kanai, Y., Cell adhesion system and human cancer morphogenesis, Cancer Sci, 94, pp. 575-81, 2003). In other words, since normal epithelial cells form a monolayer on the ECM-rich basement membrane, they can survive by effectively transducing extracellular signals from ECM. However, a loss of focal adhesion results in anoikis, leading to cell detachment from basement membrane, and consequently cell death.

Cancer cells due to multiple mutations and genomic instabilities may be allowed to disseminate from a primary tumor by abnormal alteration of cell-ECM interactions and cell-cell contacts. In the microenvironment of metastatic cancer cells, growth factors and cytokines secreted from cancer cells or neighboring fibroblasts, leukocytes, endothelial cells play an important role in cell contact, adhesion, migration, and invasion (Stamenkovic, I. Extracellular matrix remodelling: the role of matrix metalloproteinases, J Pathol, 200, pp. 448-64, 2003). Metastatic cancer cells traverse the basement membrane and stromal region to enter the circulatory systems (intravasation), and survive in the circulation. Then, they leave the circulation by extravasation. During this event, integrin-mediated adhesion of cancer cells to ECM may critically affect the metastatic potential of cells (Liotta, L. A., et al., Biochemical interactions of tumor cells with the basement membrane, Annu Rev Biochem, 55, pp. 1037-57, 1986). Among disseminated cancer cells, only cells survived anoikis may travel to distant sites via blood and lymphoid vessels, and eventually attach to a site and proliferate as metastatic tumors (Thiery, J. P., Epithelial-mesenchymal transitions in tumour progression, Nat Rev Cancer, 2, pp. 442-54, 2002).

Therefore, it would be useful to find reagent(s) to cause anoikis of tumorigenic cells without any effects on normal cells, when antitumorigenic or metastatic reagents are being screened.

TM4SF5 (or L6H) is a homolog of tumor-associated antigen L6, and forms a 4-transmembrane L6 superfamily with L6, IL-TMP, and L6D (Wright, M. D. et al., The L6 membrane proteins-a new four transmembrane superfamily, Protein Sci, 9, pp. 1594-600, 2000). TM4SF5 is highly expressed in pancreatic, gastric, colon, papilla vateri carcinoma and soft tissue sarcoma, and nonendocrine lung and ACTH (corticotropin)-negative bronchial carcinoid tumors (Pascual-Le Tallec, L. et al., Identification of genes associated with the corticotroph phenotype in bronchial carcinoid tumors, J Clin Endocrinol Metab, 87, pp. 5015-22, 2002). In the current study, we found that TM4SF5 is overexpressed in hepatocarcinoma tissues, and TM4SF5 causes actin reorganization and Epithelial-Mesenchymal Transition (EMT), leading to contact inhibition loss and oncogenic proliferation (Lee S-A et al., TM4SF5-mediated transmodulation between cytosolic p27Kip1 and Rho GTPases and epithelial-mesenchymal transition cause loss of contact inhibition, Cancer Cell, 2007). TM4SF5 overexpression in fibroblast led to actin reorganization and focal adhesion turnover (Lee, S. Y. et al., Focal adhesion and actin organization by a cross-talk of TM4SF5 with integrin α2 are regulated by serum treatment, Exp Cell Res, 312, pp. 2983-99, 2006). TM4SF (known as tetraspanin or tetraspan) proteins are a group of hydrophobic proteins of approximately 25-50 kDa with 4 transmembrane domains, and has two extracellular loops and two short cytoplasmic tails (Stipp, C. S. et al., Functional domains in tetraspanin proteins, Trends Biochem Sci, 28, pp. 106-12, 2003). TM4SFs form tetraspanin-web structures by forming complexes with cell adhesion molecules, such as integrins, to collaboratively perform their roles in cell adhesion and motility (Berditchevski, F Complexes of tetraspanins with integrins: more than meets the eye, J Cell Sci, 114, pp. 4143-51, 2001).

DISCLOSURE

Technical Problem

It is an object of the present invention to provide an anoikis-inducing agent comprising a *Tiarella polyphylla* extract, a tiarellic acid compound isolated therefrom or a pharmaceutically acceptable salt thereof, which is specific to cancer cells expressing a tumor-associated antigen L6 or a homolog thereof.

It is another object of the present invention to provide a pharmaceutical composition for treating and preventing cancer diseases and a functional health food for preventing and improving cancer diseases, comprising the anoikis-inducing agent.

BEST MODE

Figure 1:
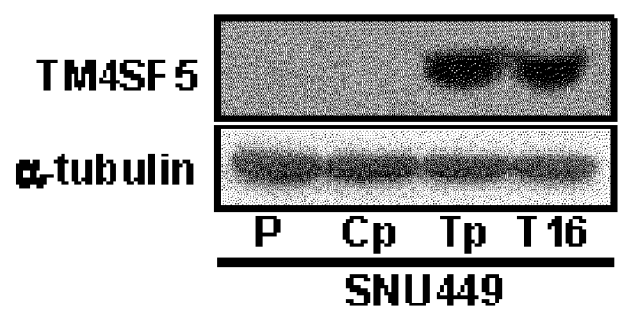
FIG. 1 shows TM4SF5 expression of TM4SF5-null parental SNU449 cell (Hereinbelow, referred to as 'P'), stable control SNU449 cell (Hereinbelow, referred to as 'Cp'), stable TM4SF5-overexpressing SNU449Tp cell (Hereinbelow, referred to as 'Tp'), and SNU449T16 cell (Hereinbelow, referred to as 'T16')

In one aspect, the present invention relates to an anoikis-inducing agent comprising a *Tiarella polyphylla* extract, a tiarellic acid compound isolated therefrom or a pharmaceutically acceptable salt thereof, which is specific to cancer cells expressing a tumor-associated antigen L6 or a homolog thereof.

As used herein, *Tiarella polyphylla* D. Don, also known as a medicinal herb for treatment of asthma, is a perennial herb belonging to the family Saxifragaceae. It inhabits only on the summit of Ullung Island in Korea. The *Tiarella polyphylla* extract of the present invention is a crude extract or a polar solvent soluble extract from *Tiarella polyphylla*. The crude extract includes an extract being soluble in a solvent selected from the group consisting of water including purified water, C1-C4 lower alcohol, and the mixtures thereof, preferably a methanol soluble extract. In addition, the polar solvent soluble extract includes an extract being soluble in a solvent selected from the group consisting of water, methanol, ethanol, butanol, and the mixtures thereof, preferably butanol.

The *Tiarella polyphylla* extract of the present invention may be prepared by a method well known to those skilled in the art. For example, the whole plant of *Tiarella polyphylla* is collected, and dried in the shade, and then pulverized. Then, the powder of *Tiarella polyphylla* is mixed with 2 to 20-fold volume of polar solvent, for example, water, $C_1$-$C_4$ lower alcohol such as methanol, ethanol, and butanol, or a mixed solvent thereof having a mixing ratio of about 1:0.1 to 1:10, preferably methanol, and was extracted at the temperature ranging from 20 to 50° C. for the period ranging 10 hrs to 48 days, preferably 20 to 30 hrs, by hot water extraction, cold water extraction, reflux extraction with cold water, or ultrasonication extraction two to five times, preferably two to three times. The resultant is filtered, concentrated, and dried according to ordinary methods to obtain a crude extract. In addition, the crude extract is suspended in distilled water, and then mixed with 1 to 100-fold, preferably 1 to 5-fold volume of polar solvent such as water, ethanol, methanol, and butanol, and extracted once to ten times, preferably once to five time to obtain a polar solvent soluble extract. A conventional fractionation process may be additionally performed (Harborne J. B., A guide to modern techniques of plant analysis. 3, pp 6-7, 1998).

A tiarellic acid compound [3,23-dihydroxy-20(29)-lupen-27-oic acid] isolated from the *Tiarella polyphylla* extract of the present invention is represented by the following Formula (I).

[Formula 1]

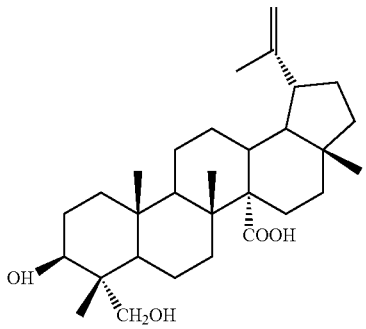

(I)

The tiarellic acid compound may be isolated from the *Tiarella polyphylla* extract by a method known to those skilled in the art. For example, the *Tiarella polyphylla* extract of the present invention is suspended in distilled water, and then extracted with hexane to obtain a hexane soluble fraction. The hexane soluble fraction is then subjected to a silica gel column chromatography and eluted with a hexane-chloroform-methanol mixture to obtain fractions. The fraction containing tiarellic acid is repeatedly subjected to a column chromatography. The fraction containing high purity of tiarellic acid is subjected to a solvent recrystallization to give a pure tiarellic acid of the present invention.

As used therein, the term "pharmaceutically acceptable salt" refers to those derived from pharmaceutically or physiologically acceptable inorganic and organic acids and bases. Examples of suitable acid include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfuric acid, tartaric acid, acetic acid, citric acid, methanesulfonic acid, formic acid, benzoic acid, malonic acid, naphthalene-2-sulfonic acid, and benzenesulfonic acid. Examples of salt derived from suitable base may include an alkali metal such as sodium, and an alkaline earth metal such as magnesium and ammonium.

The *Tiarella polyphylla* extract, the tiarellic acid compound isolated therefrom or the pharmaceutically acceptable salt thereof of the present invention specifically affects cancer cells expressing a tumor-associated antigen L6 or a homolog thereof to induce anoikis of cancer cells.

As used herein, the term, "a tumor-associated antigen L6 or a homolog thereof" refers to a protein which forms a transmembrane L6 superfamily, induces uncontrolled cell growth and is expressed in diverse tumor cells. The tumor-associated antigen L6 or a homolog thereof includes L6, TM4SF5 (or L6H; Transmembrane 4 L6 family member 5), IL-TMP, and L6D, preferably TM4SF5.

As used herein, the term "anoikis" refers to a specialized form of apoptosis, resulting from the loss of cell attachment to extracellular matrix or inappropriate cell adhesion to extracellular matrix. For the sake of convenience, anoikis can be described as cell death or apoptosis in the present invention.

In a specific embodiment of the present invention, searching for a compound which inhibits cell proliferation due to a homolog of tumor-associated antigen L6, TM4SF5, the present inventors found that tiarellic acid (3,23-dihydroxy-20 (29)-lupen-27-oic acid) induces anoikis in cell lines expressing TM4SF5. When TM4SF5-expressing cell lines were treated with tiarellic acid (TA), phosphorylation of focal adhesion molecules was inhibited, leading to loss of cell attachment. Thus, cell proliferation was inhibited, resulting in anoikis. In addition, TA administration inhibited TM4SF5-mediated tumorigenesis in nude mice. These observations suggest that tiarellic acid (TA) may be developed as a putative therapeutic reagent against TM4SF5-positive tumorigenesis.

The cancer cells expressing a tumor-associated antigen L6 or a homolog thereof are known to cause liver cancer, gastric cancer, colon cancer, breast cancer, lung cancer, non-small cell lung cancer, bone cancer, pancreatic cancer, skin cancer, head or neck cancer, cutaneous or ocular melanoma, uterine cancer, ovarian cancer, large intestine cancer, small intestine cancer, rectal cancer, anal cancer, fallopian tube carcinoma, endometrial carcinoma, cervical carcinoma, vaginal carcinoma, vulvar carcinoma, Hodgkin's disease, esophageal cancer, small intestine cancer, malignant lymphoma, bladder cancer, gallbladder cancer, endocrine gland cancer, thyroid cancer, parathyroid cancer, adrenal cancer, soft-tissue sarcoma, urinary cancer, penis cancer, prostate cancer, chronic or acute leukemia, lymphocyte lymphoma, bladder cancer, kidney or ureter cancer, renal cell carcinoma, renal pelvic carcinoma, central nervous system tumor, primary central nervous system lymphoma, spinal tumor, brain stem glioma, or pituitary adenoma, preferably liver cancer, pancreatic cancer, gastric cancer, colon cancer, papillary cancer, soft-tissue sarcoma, nonendocrine lung tumor, or ACTH-negative bronchial carcinoid tumor.

In another aspect, the present invention provides a pharmaceutical composition for preventing and treating cancer diseases comprising the anoikis-inducing agent containing a *Tiarella polyphylla* extract, a tiarellic acid compound isolated therefrom, or a pharmaceutically acceptable salt thereof, which is specific to cancer cells expressing a tumor-associated antigen L6 or a homolog thereof, as an active ingredient.

The composition for preventing and treating cancer diseases of the present invention includes 0.1 to 50% by weight of the anoikis-inducing agent comprising a *Tiarella polyphylla* extract, a tiarellic acid compound isolated therefrom or a pharmaceutically acceptable salt thereof, based on the total weight of the composition.

The pharmaceutical composition of the present invention may further include suitable carriers, excipients, and diluents which are generally used in the preparation of pharmaceutical composition.

According to conventional methods, the pharmaceutical composition of the present invention may be formulated into an oral preparation such as a powder, a granule, a tablet, a capsule, a suspension, an emulsion, a syrup, and an aerosol, an external preparation, suppository, or a sterilized injectable solution. The carriers, excipients and diluents contained in the composition may be exemplified by lactose, dextrose, sucrose, sorbitol, mannitol, xylitol, erythritol, maltitol, starches, acacia rubber, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate and mineral oil. Such preparations may be prepared using diluents or excipients ordinarily employed, such as filler, extender, binder, wetting agent, disintegrating agent, and surfactant. Examples of the solid preparation for oral administration include a tablet, a pill, a powder, a granule, and a capsule, and the solid preparation maybe prepared by mixing the compound with at least one excipient such as starch, calcium carbonate, sucrose, lactose, and gelatin. Further, in addition to the excipients, lubricants such as magnesium stearate and talc may be used. Examples of a liquid preparation for oral administration include a suspension, a liquid for internal use, an emulsion, and a syrup, and various excipients such as wetting agent, sweetener, flavor, and preservative may be contained, in addition to general diluents such as water and liquid paraffin. Examples of the preparation for parenteral administration include an aseptic aqueous solution, a non-aqueous solvent, a suspension, an emulsion, a lyophilized agent, and suppository. As the non-aqueous solvent and suspension, propylene glycol, polyethylene glycol, plant oil such as olive oil, injectable ester such as ethyloleate or the like may be used. As a suppository base, witepsol, macrogol, tween 61, cacao butter, lauric butter, glycerogelatin or the like may be used.

An effective dosage of the pharmaceutical composition in the present invention may be determined depending on the patient's health state and body weight, severity of the diseases, drug formulation, administration routes, and administration time, and may be suitably selected by those skilled in the art. However, for better efficacy, the composition of the present invention may be administered at a daily dosage of 0.0001 to 100 mg/kg, preferably 0.001 to 10 mg/kg once or several times. The dosage is not intended to limit the scope of the present invention.

The pharmaceutical composition of the present invention may be administered to mammals such as rat, mouse, livestock, and human via various routes. All modes of administration are contemplated, for example, administration can be made orally, rectally or by intravenous, intramuscular, subcutaneous, intraepidural or intracerebroventricular injection.

In still another aspect, the present invention relates to a method for treating and preventing cancer diseases caused by cancer cells expressing a tumor-associated antigen L6 or a homolog thereof, comprising the step of administering the anoikis-inducing agent containing a *Tiarella polyphylla* extract, a tiarellic acid compound isolated therefrom, or a pharmaceutically acceptable salt thereof, which is specific to cancer cells expressing a tumor-associated antigen L6 or a homolog thereof, or administering a pharmaceutical composition for treating and preventing cancer diseases comprising the same, to a subject with cancer.

In accordance with the cancer cell-specific anoikis-inducing agent or pharmaceutical composition of the present invention, its efficacy, administration method, and dosage are the same as described above. In the method of the present invention, the term "subject" encompasses mammals such as human, monkey, mouse, swine, cattle and rabbit, but is not limited thereto.

In still another aspect, the present invention provides a functional health food, comprising the anoikis-inducing agent containing a *Tiarella polyphylla* extract, a tiarellic acid compound isolated therefrom, or a pharmaceutically acceptable salt thereof, which is specific to cancer cells expressing a tumor-associated antigen L6 or a homolog thereof, as an active ingredient. The food comprising the cancer cell-specific anoikis-inducing agent as an active ingredient includes, but is not limited to, various foods, beverages, gums, tea, vitamin complex, and health improving foods.

The cancer cell-specific anoikis-inducing agent, which contains a *Tiarella polyphylla* extract, a tiarellic acid compound isolated therefrom, or a pharmaceutically acceptable salt thereof, may be contained in am amount of 0.01 to 15% by weight, based on the total weight of the food, and added in am amount of 0.02 to 5 g, preferably 0.3 to 1 g, based on 100 ml of the health drink composition.

The functional health food of the present invention may be in the form of tablet, capsule, pill, liquid formulations or the like.

Health drink composition of the present invention is not limited to any specific composition insofar as it is a liquid containing the above compound as essential ingredients in the indicated proportions, like ordinary beverages and may contain various sweeteners or natural carbohydrates as additional ingredients. Examples of the natural carbohydrates described above may include monosaccharide such as glucose and fructose, disaccharides such as maltose and sucrose, polysaccharides such as dextrin and cyclodextrin, and sugar alcohols such as xylitol, sorbitol and erythritol. As the sweeteners other than those mentioned above, natural sweeteners (thaumatine, stevia extract (e.g. rebaudioside A), glycyrrhizin), and synthetic sweeteners (saccharin, aspartame) can be used with advantage. The proportion of said natural carbohydrate is generally about 1 to 20 g, preferably about 5 to 12 g, per 100 ml of the composition of the invention.

Aside from the above, the functional health food of the invention may contain various nutrients, vitamins, minerals (electrolytes), flavors such as synthetic flavors and natural flavors, coloring matter and enhancer (cheese, chocolate), pectic acid and its salts, alginic acid and its salts, organic acids, protective colloid thickeners, pH control agents, stabilizers, preservatives, glycerins, alcohols, and carbonating agents for carbonated beverage use. In addition, the functional health food of the present invention may contain natural fruit juices and fruit pulps for the provision of fruit juice drinks and vegetable drinks. These ingredients can be used independently or in combination. The proportion of these additives is not so critical but can be generally selected from the range of 0 to about 20 parts by weight per 100 parts by weight of the compound of the present invention.

Hereinafter, the present invention will be described in more detail with reference to Examples and Experimental Examples. However, these Examples and Experimental Examples are for illustrative purposes only, and the invention is not intended to be limited by these Examples and Experimental Examples.

MODE FOR INVENTION

Example 1

Preparation of *Tiarella polyphylla* Crude Extract

The whole plant of *Tiarella polyphylla* was collected in Ullung Island, Korea and 1.1 kg thereof was dried, pulverized, and mixed with 5 L of methanol. The mixture was stirred at room temperature for 24 hours, and filtered under vacuum to recover the supernatant. The procedure was repeated twice to collect the supernatant. Then, the supernatant was concentrated under reduced pressure to obtain 100.5 g of methanol crude extract of *Tiarella polyphylla*.

Example 2

Preparation of Polar Solvent Soluble *Tiarella polyphylla* Extract

The *Tiarella polyphylla* crude extract obtained in Example 1 was suspended in 1 L of distilled water. 1 L of butanol was added thereto, and mixed to divide into a butanol soluble fraction and a water soluble fraction, followed by filtration and concentration under reduced pressure to remove the solvent. Finally, 80.0 g of butanol soluble *Tiarella polyphylla* extract was obtained to use as a sample in the following experiments.

Example 3

Isolation of Tiarellic Acid from *Tiarella polyphylla* Extract 3.29 kg of *Tiarella polyphylla* was extracted with 64 L of methanol four times at room temperature for 7 days, followed by concentration under reduced pressure to obtain 3.52 kg of methanol extract. 3.52 kg of methanol extract was suspended in 10 L of water, and then repeatedly extracted with 30 L of hexane three times to obtain 651 g of hexane soluble fraction. The filtrate was repeatedly extracted with 30 L of ethyl acetate three times to obtain 510 g of ethyl acetate soluble extract. In addition, after ethyl acetate extraction, 40 L of the residual suspension was put into Diaion HP-20, and eluted with 80 L of water. The water soluble fraction was freeze-dried to obtain 1.4 kg, and then eluted with 80 L of 50% methanol. The 50% methanol soluble fraction was freeze-dried to obtain 792 g. Finally, the Diaion HP-20 column was eluted with methanol to 158 g of methanol soluble fraction. Each fraction of *Tiarella polyphylla* extract was subjected to thin layer chromatography. As a result, the hexane soluble fraction was found to contain a large amount of tiarellic acid. 330 g, half amount of the hexane soluble fraction was added to 4 kg of silica gel, and then eluted with hexane-ethyl acetate (10:1, 13.2 L; 5:1, 16.8 L; 2:1, 24 L), chloroform-methanol (9:1, 36 L), chloroform-methanol-water (7:3:0.1, 20 L), and 12 L of methanol, successively to yield 9 fractions. By performing thin layer chromatography, tiarellic acid was found in fractions 6 and 7. Two fractions containing tiarellic acid were put together, and applied to 2 kg of silica gel, followed by elution with chloroform-methanol (20:1, 18.9 L; 7:1, 9 L; 3:1, 4 L) and 9 L of methanol to yield 11 fractions. Among them, tiarellic acid was found in fractions 4, 5, and 6. These fractions were applied to silica gel column, and subjected to solvent recrystallization to obtain 2 g of tiarellic acid. In addition, 330 g of the hexane soluble fraction was partitioned by the above method to obtain 2 g of tiarellic acid. Total 4 g of tiarellic acid having following physical properties were isolated and purified (Hereinbelow, referred to as TA).

Needles (MeOH);

mp 254-256C;

[a] 2 3 D+94 (pyridine, c 0.14);

IR (KBr, cm-1): 3491 (OH), 1689 (CO), 1645 (C=C), 1450, 1388, 1262, 1222, 1044; HRMS m/z 472.3552 (M+, Calcd for C30H4804: 472.3553);

EIMS (rel. int.) m/z: 472 [M]+ (61), 454 [M-H2O]+ (34), 436 [M-2H2O]+ (62), 424 (42), 396 (26), 205 (75), 187 (71), 175 (87), 173 (100);

13C-NMR (150 MHz, pyridine-d5): 13.0 (C-24), 17.4 (C-25), 17.5 (C-26), 18.7 (C-6), 18.8 (C-28), 19.4 (C-30), 21.3 (C-11), 25.8 (C-15), 26.7 (C-12), 27.9 (C-2), 30.1 (C-21), 37.7 (C-10), 38.2 (C-7), 38.3 (C-16), 39.2 (C-1), 39.6 (C-13), 40.4 (C-22), 40.8 (C-8), 42.9 (C-4), 43.0 (C-17), 48.1 (C-19), 49.2 (C-5), 51.4 (C-18), 51.6 (C-9), 60.4 (C-14), 68.2 (C-23), 73.6 (C-3), 110.2 (C-29), 150.9 (C-20), 178.3 (C-27);

1H-NMR (600 MHz, pyridine-d5): 1.05, 1.71 (2H, m, each, H-1), 1.82, 1.91 (2H, m, each, H-2), 4.02 (1H, dd, J=4.7, 11.6 Hz, H-3), 1.51 (1H, dd, J=1.5, 12.0 Hz, H-5), 1.48, 1.65 (2H, m, each, H-6), 1.87, 2.06 (2H, m, each, H-7), 2.02 (1H, dd, J=1.7, 12.7 Hz, H-9), 1.32, 1.64 (2H, m, each, H-11), 1.87, 2.60 (2H, m, each, H-12), 1.88 (1H, m, H-13), 1.67, 2.28 (2H, m, each, H-15), 1.70, 1.78 (2H, m, each, H-16), 1.81 (1H, m, H-18), 2.60 (1H, m, H-19), 1.36, 1.97 (2H, m, each, H-21), 1.16, 1.40 (2H, m, each, H-22), 3.57, 4.07 (2H, d, J=10.4, each, H-23), 1.04 (3H, s, H-24), 1.01 (3H, s, H-25), 1.21 (3H, s, H-26), 0.90 (1H, s, H-28). 4.76, 4.96 (2H, s, each, H-29), 1.86 (3H, d, J=6.4 Hz, H-30).

Reference Example 1

Cell Culture

After virus infection, pooled stable clones (control SNU449Cp and TM4SF5-expressing SNU449Tp cell clones) and single cell-driven stable clones (TM4SF5-expressing SNU449T16) were prepared by infecting SNU449 hepatocytes (Korean Cell Bank, Seoul, Korea) with retrovirus for empty pLNCX or pLNCX with TM4SF5. Parental and control cells (Cp) were maintained in RPMI-1640/10% FBS/0.25 μg/ml gentamycin (Calbiochem, San Diego, Calif.) without or with 200 μg/ml G418 (A.G. Scientific Inc., San Diego, Calif.), respectively, at 37° C. and 5% CO2. Cells endogenously expressing TM4SF5 or cells endogenously expressing no TM4SF5 (Korean Cell Bank) were maintained in either DMEM-H or RPMI-1640 media with 10% FBS (JBI Inc., Daegu, Korea).

Reference Example 2

Preparation of Cell Lysates and Western Blot

Whole cell lysates from cells under diverse experimental conditions were prepared, as described in the literature (Lee, S. Y. et al., Focal adhesion and actin organization by a cross-talk of TM4SF5 with integrin α2 are regulated by serum treatment, Exp Cell Res, 312, pp. 2983-99, 2006). For example, cells were subjected to electroporation (950 μF, 250 V) with a control GFP, wild-type focal adhesion kinase (FAK), paxillin, p130Cas cDNA. One day after electroporation, cells were treated with TA (20 μM) for the indicated periods. Cells cultured normally or treated with TA at different concentrations for the indicated periods were harvested using RIPA buffer. Control or tumor tissues from nude mice were frozen immediately after surgery using liquid $N_2$. Tissues in the liquid $N_2$ was homogenized using a mortar and pestle, and extracted using 0.1% SDS containing RIPA buffer. Standard Western blots of lysates were performed by using antibody against phospho-$Y^{397}$, $Y^{407}$, $Y^{577}$, $Y^{861}$, $Y^{925}$ FAK (BioSource International, Inc., Camarillo, Calif.), phospho-$Y^{416}$Src, c-Src, p15$^{INK4B}$, p16$^{INK4A}$ (Santa Cruz Biotech., Santa Cruz, Calif.), FAK, p130Cas, paxillin, p$Y^{118}$paxillin, active caspase-3 (BD Transduct. Lab., San Jose, Calif.), α-tubulin (Sigma, St Louis, Mo.), phopsho-$S^{473}$, or $T^{308}$Akt, Akt, phospho-Erk1/2, Erk1/2 (Cell Signaling Tech., Danvers, Mass.), and TM4SF5 (homemade).

Reference Example 3

Immunofluorescence Microscopy

Cells were treated with DMSO or 20 μM TA for 24 hrs. Then, the cells were plated on 10 μg/ml fibronectin-precoated coverslips and incubated for 2 hrs in the presence of DMSO or 20 μM TA. Subsequently, immunofluorescence staining was performed using p$Y^{397}$ FAK, p$Y^{118}$ paxillin, and actin, as described in the literature (Lee, S. Y. et al., Focal adhesion and actin organization by a cross-talk of TM4SF5 with integrin α2 are regulated by serum treatment, Exp Cell Res, 312, pp. 2983-99, 2006). Mounted samples were visualized by a fluorescent microscope (BX51, Olympus, Japan).

Reference Example 4

Preparation of Experimental Animal 4-5 week old female nude mice (BALB/cAnNCrjBgi-nu) were purchased from Orient. Co. Ltd. (Seongnam, Korea). The mice were housed in a specific pathogen-free room under controlled temperature and humidity. All animal procedures were performed in accordance with the procedures in Seoul National University Laboratory Animal Maintenance Manual and with IRB agreement. Mice aged 5-6 weeks were injected subcutaneously with $5 \times 10^6$ viable SNU449Cp or SNU449T16 cells. Tumor volumes were measured with a caliper and calculated using the following Mathematical Formula 1. When the tumor volume reached 200 mm³, mice were injected intraperitoneally with 3 mg/kg or 30 mg/kg (body weight) of tiarellic acid (TA) every other day for 30 days.

(Width×Length²)/2    [Mathematical Formula 1]

Width: minimal diameter (mm)
Length: maximal diameter (mm)

Experimental Example 1

Inhibitory Effect on Growth of TM4SF5-Expressing Cell

To measure the inhibitory effect of tiarellic acid (TA) obtained in Example 3 on growth of TM4SF5-expressing cell, the following procedure was performed, as described in the literature (Lee, S. Y. et al., Focal adhesion and actin organization by a cross-talk of TM4SF5 with integrin α2 are regulated by serum treatment, Exp Cell Res, 312, pp. 2983-99, 2006).

TM4SF5-null parental SNU449 (Hereinbelow, referred to as 'P'), stable control SNU449 (Hereinbelow, referred to as 'Cp'), stable TM4SF5-overexpressing SNU449Tp (Hereinbelow, referred to as 'Tp'), and SNU449T16 (Hereinbelow, referred to as 'T16') cultured by the method of Reference Example 1 were treated with tiarellic acid (TA) at varying concentrations (0, 0.1, 5, 20 μM), and the inhibitory effect on cell growth was measured. The results are shown in FIGS. 1 to 4, respectively.

Figure 2:
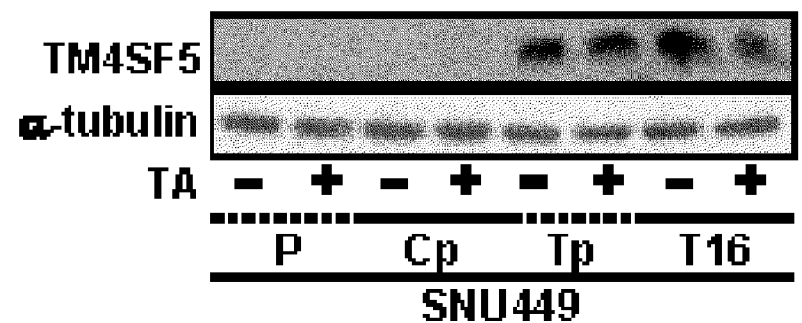
FIG. 2 shows the effect of tiarellic acid (TA) treatment on TM4SF5 expression of P, Cp, Tp and T16 cells.

As shown in FIGS. 1 and 2, it was found that tiarellic acid (TA) exhibited the inhibitory effect on the growth of TM4SF5-expressing cell, without affecting the expression level of TM4SF5 (see FIGS. 1 and 2).

Figure 3:
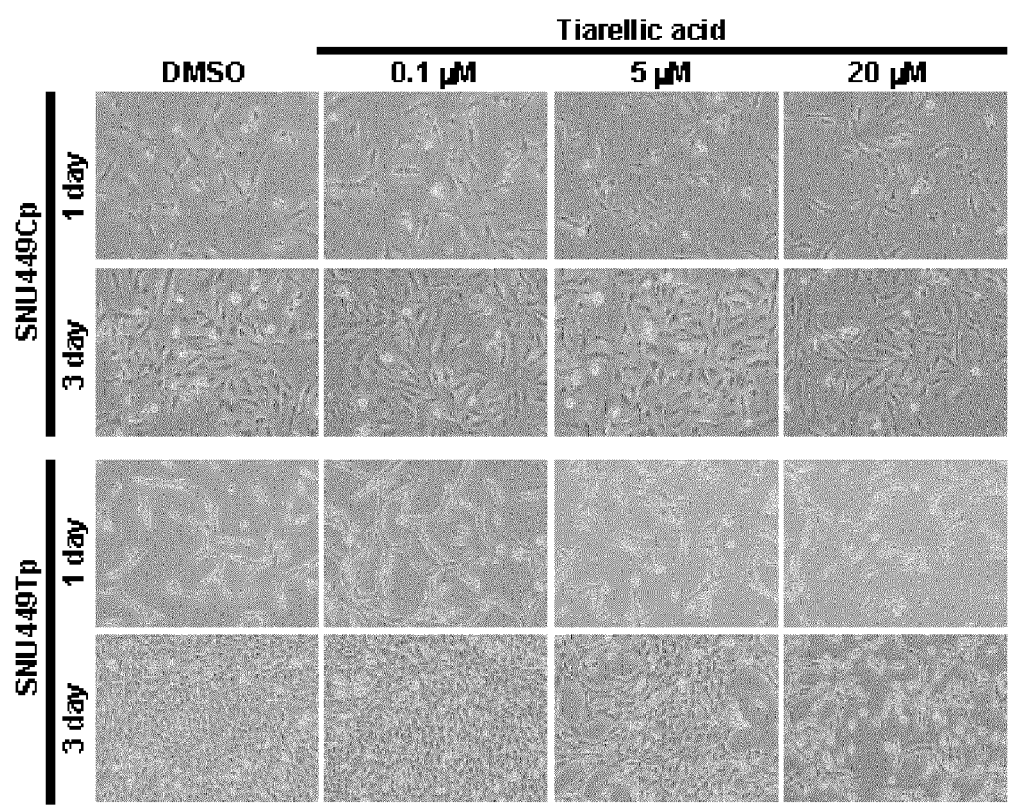
FIG. 3 is a microscopic photograph showing changes in growth of SNU449Cp and SNU449Tp cells, depending on the concentration of tiarellic acid (TA)
Figure 4:
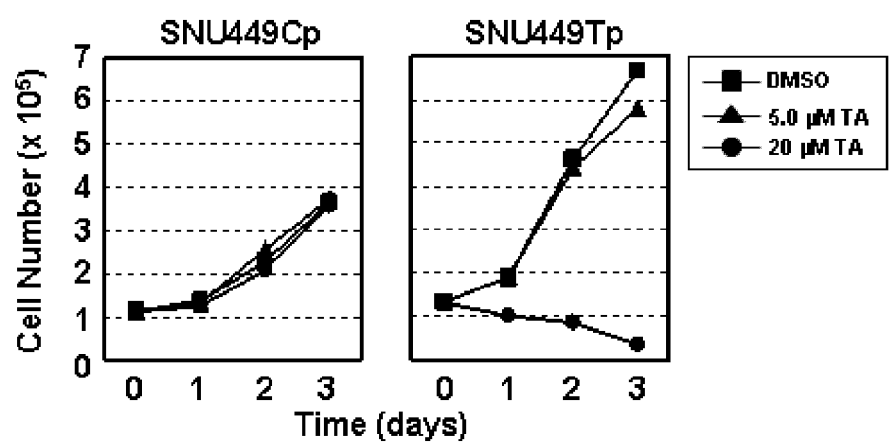
FIG. 4 is a graph showing the number of SNU449Cp and SNU449Tp cells, depending on the concentration of tiarellic acid (TA) and time.

In addition, as shown in FIGS. 3 and 4, when the TM4SF5 null SNU449Cp cells were treated with 20 μM tiarellic acid (TA) for 3 days, the inhibitory effect was not observed. On the other hand, when TM4SF5-expressing SNU449Tp cells were treated with tiarellic acid (TA) for 3 days, the inhibitory effect was observed at a low concentration of 5 μM, and reduced cell density and round shaped cells were observed at a concentration of 20 μM (see FIG. 3). As shown in FIG. 4, TA treatment decreased the number of TM4SF5-expressing cells, suggesting that the inhibitory effect is due to apoptosis (see FIG. 4).

Figure 5:
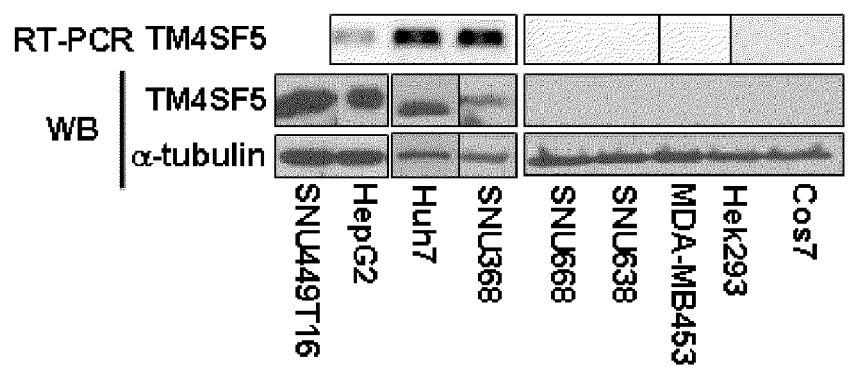
FIG. 5 shows TM4SF5 expression in diverse cell lines.

Next, to confirm that tiarellic acid (TA) is specific to TM4SF5, cytotoxicity of tiarellic acid (TA) was examined using cells with endogenous TM4SF5 expression. RT-PCR was performed using a primer set described in the following Table 1 under the conditions including 30 cycles of 94° C. for 30 sec, 55° C. for 30 sec, and 72° C. for 30 sec. The results are shown in FIG. 5 (see FIG. 5). Diverse cell lines were treated with tiarellic acid (TA) at a concentration of 5 or 20 μM.

TABLE 1

| | Sequence |
|---|---|
| Forward primer (SEQ ID NO. 1) | 5'-ATG TGT ACG GGA AAA TGT GCC CGC T-3' |
| Reverse primer (SEQ ID NO. 2) | 5'-AGT GAG GTG TGT CCT GTT TTT TC-3' |

Figure 6:
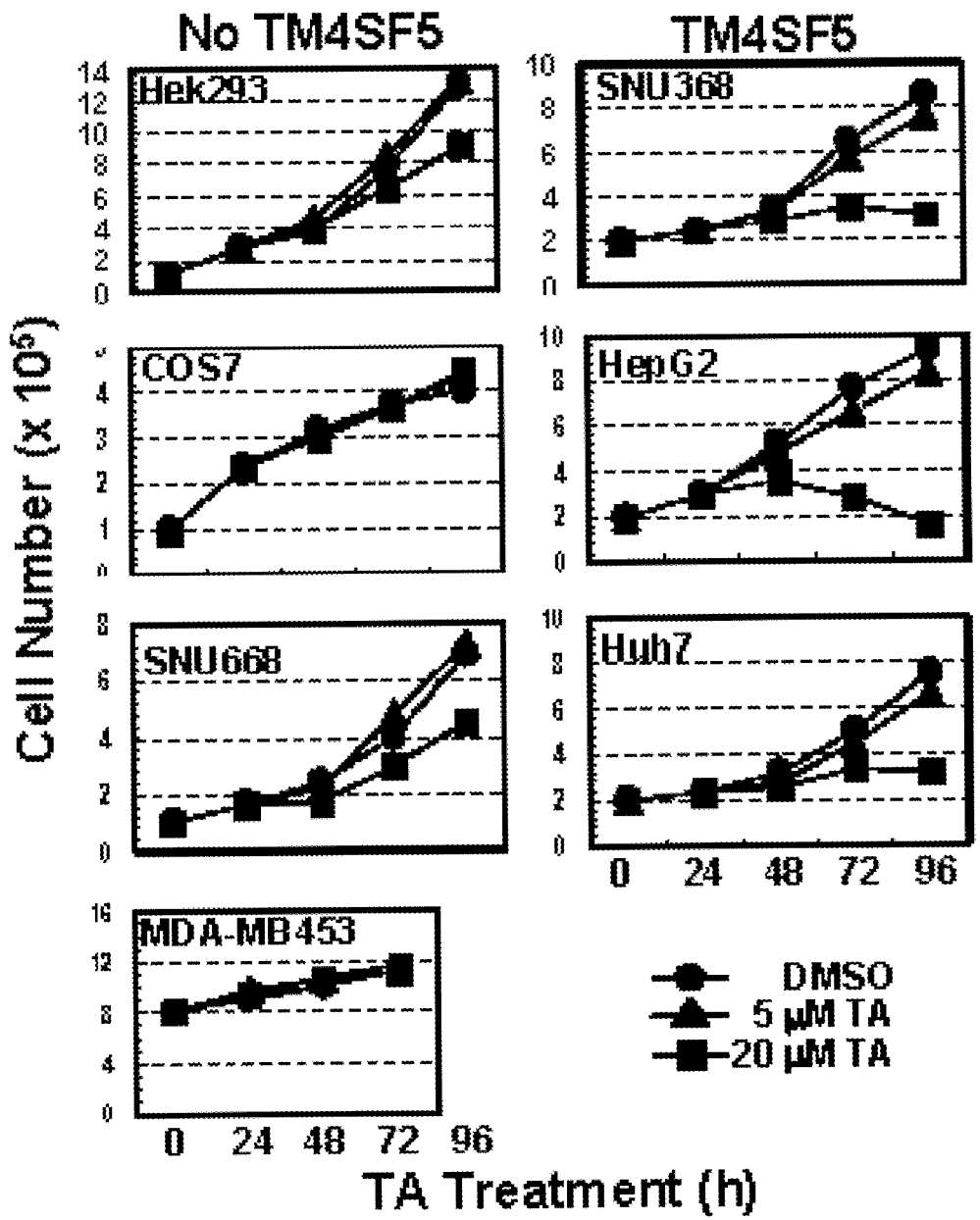
FIG. 6 is a graph showing the number of diverse cell lines with or without TM4SF5, after tiarellic acid (TA) treatment.
Figure 7:
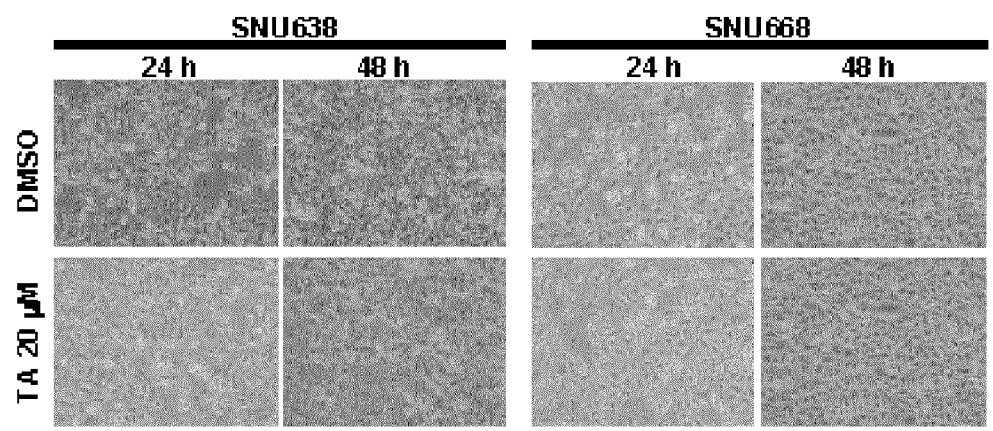
FIG. 7 is a microscopic photograph showing the expression and activation of focal adhesion molecules in TM4SF5-null cells (SNU638 and SNU668), after tiarellic acid (TA) treatment.

As a result, TM4SF5-null cells including Hek293 and COST fibroblast, MDA-MB-453 breast, SNU638 and SNU668 stomach, and SNU398 liver epithelial cells were found to proliferate with time. Thus, it can be seen that these cells were not affected by tiarellic acid (TA). However, cells with endogenous TM4SF5 expression showed growth suppression after TA treatment, leading to the eventual decrease in cell number (see FIGS. 6 and 7).

Consequently, it can be seen that the above result is in connection with those of SNU449Tp ectopically expressing TM4SF5.

Experimental Example 2

Tiarellic Acid (TA)-Mediated Inhibition of Focal Adhesion Molecule Activation To examine which signaling molecule is affected by tiarellic acid (TA), the following procedure was performed, as described in the literature (Lee, S. Y. et al., Focal adhesion and actin organization by a cross-talk of TM4SF5 with integrin α2 are regulated by serum treatment, Exp Cell Res, 312, pp. 2983-99, 2006).

The SNU449 cell lines were treated with tiarellic acid (TA) in a dose- (0, 1, 5, 20 μM) and time-dependent (0, 8, 16, 24, 36 hrs) manner.

The SNU449Cp and SNU449T16 cell lines were treated with tiarellic acid (TA) at varying concentrations (0, 1, 5, 20 μM) for 24 hrs, and then immunoblot assay was performed.

Figure 8:
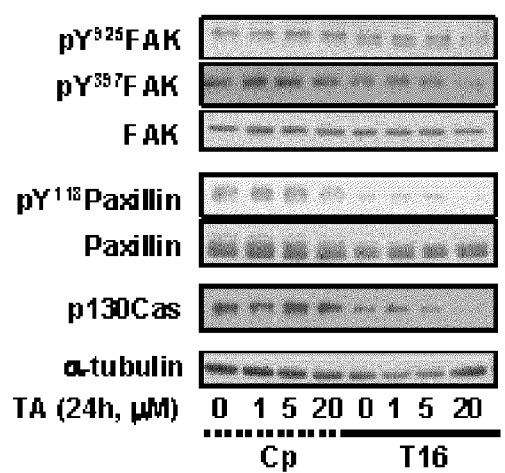
FIG. 8 shows the result of immunoblot assay, in which the expression and activation of focal adhesion molecules are examined in cell lines treated with tiarellic acid (TA) at varying concentrations.
Figure 9:
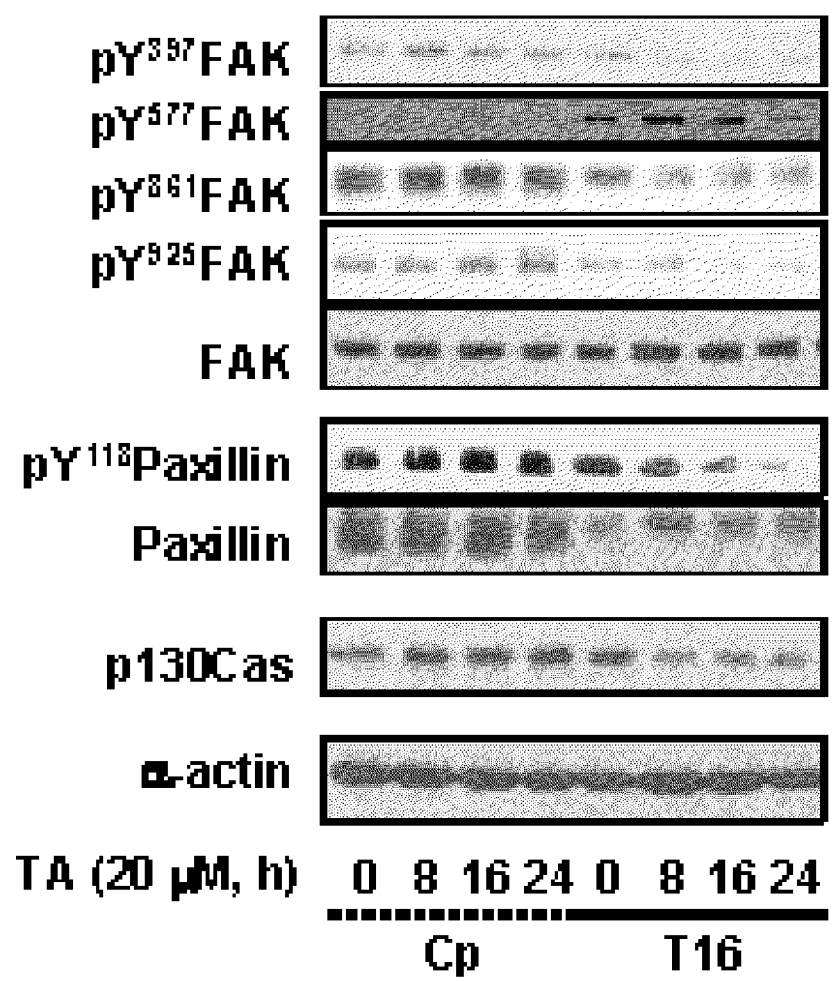
FIG. 9 shows the result of immunoblot assay, in which the expression and activation of focal adhesion molecules are examined in cell lines treated with tiarellic acid (TA) for various time periods.
Figure 10:
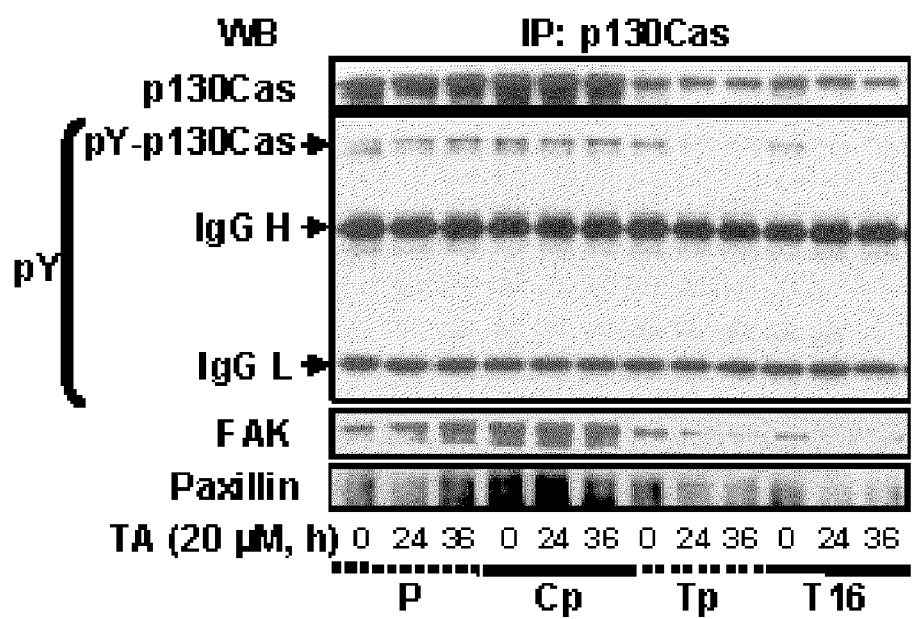
FIG. 10 shows p130Cas phosphorylation level and physical association among p130Cas, FAK and paxillin, after tiarellic acid (TA) treatment.
Figure 11:
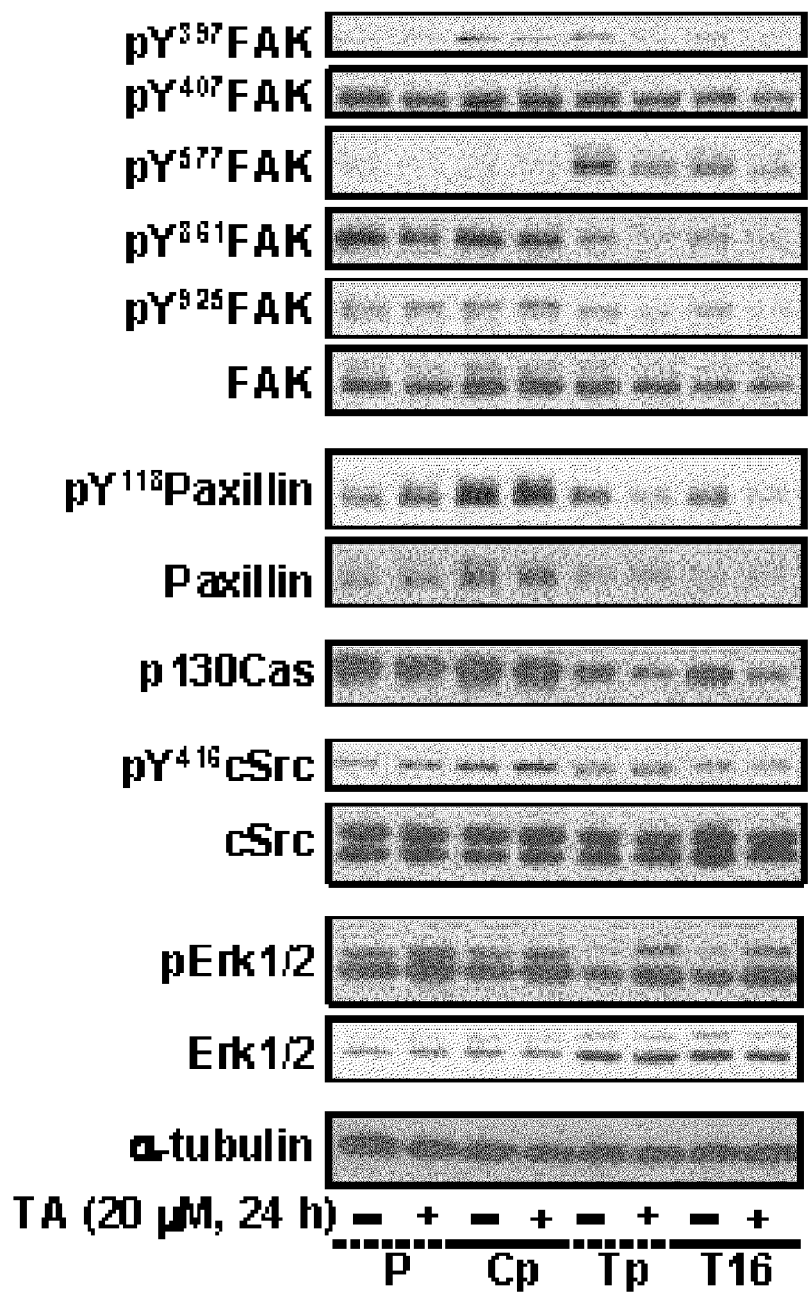
FIG. 11 shows the expression and activation of focal adhesion molecules in SNU449 cell lines, after tiarellic acid (TA) treatment.
Figure 12:
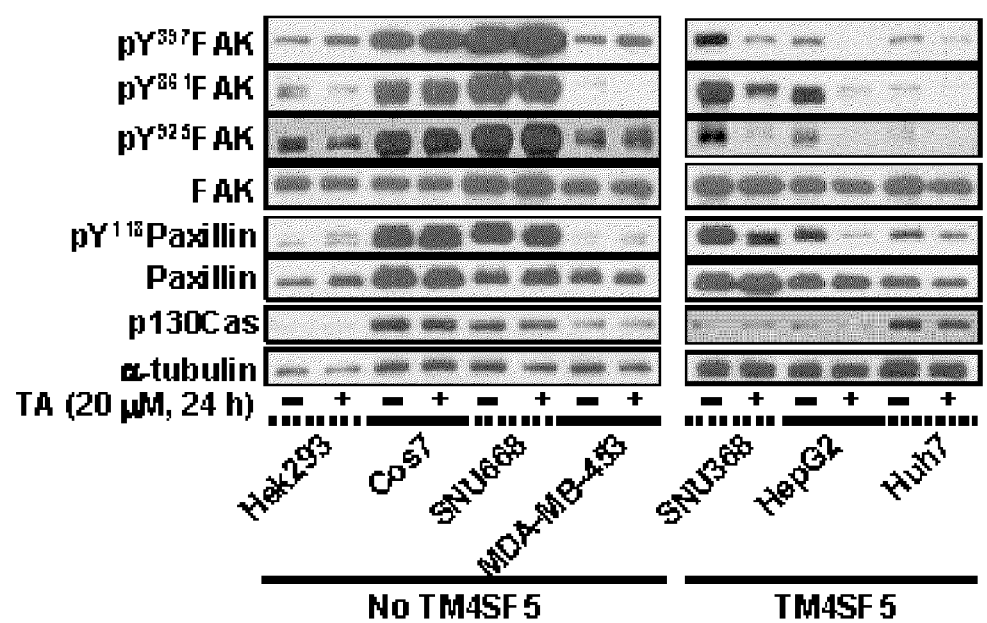
FIG. 12 shows the expression and activation of focal adhesion molecules in diverse cell lines with or without TM4SF5, after tiarellic acid (TA) treatment.

As shown in FIG. 8, in the TM4SF5-expressing SNU449T16 cells treated with 20 μM TA, reduced focal adhesion kinase (FAK) and paxillin phosphorylations and p130Cas protein levels were observed, whereas no effect was observed in SNU449Cp cells expressing no TM4SF5 (see FIG. 8). Also, in the SNU449T16 cells treated with 20 μM TA, FAK and paxillin phosphorylation and p130Cas protein levels were remarkably decreased in a time-dependent manner (see FIG. 9). In addition, it can be seen that tiarellic acid (TA) treatment decreased p130Cas phosphorylation and the physical association among focal adhesion kinase (FAK), p130Cas, and paxillin (see FIG. 10). Furthermore, the TM4SF5-dependent inhibitory effects of tiarellic acid (TA) were observed in TM4SF5-expressing SNU449Tp cell line (see FIG. 11). Theses observations indicate that tiarellic acid (TA) treatment affected phosphorylation and complex formation of focal adhesion molecules only in TM4SF5-expressing cells. In addition, tiarellic acid (TA)-mediated effects on focal adhesion molecule activation were examined in cells that express endogenous TM4SF5 and in null cell lines. Interestingly, the inhibitory effects of TA treatment on focal adhesion molecule activation were observed also in cells endogenously expressing, but not lacking, TM4SF5 (see FIG. 12). However, as shown in the above result (see FIG. 11), it was found that tiarellic acid (TA) treatment slightly increased pErk1/2 in both SNU449Cp and SNU449Tp.

Figure 13:
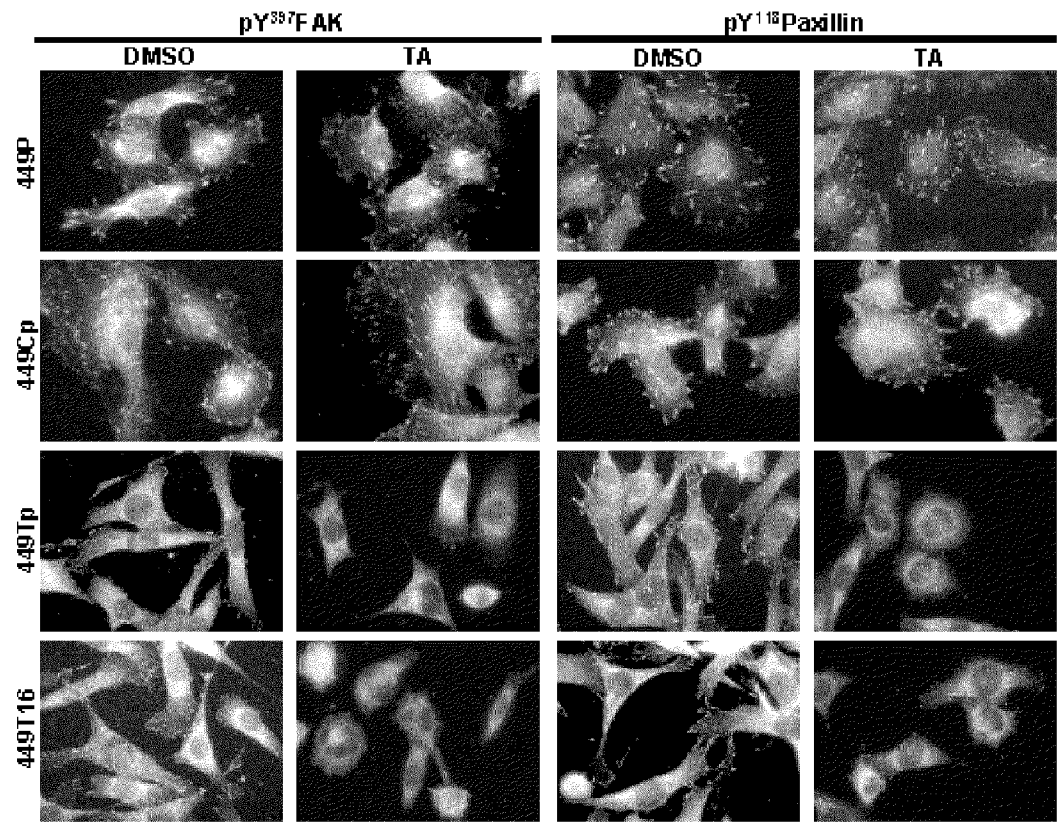
FIG. 13 is the result of analyzing focal adhesion formation by performing immunostaining for pY397FAK (focal adhesion kinase) and pY118 paxillin, after tiarellic acid (TA) treatment.
Figure 14:
FIG. 14 shows a dissociation between integrin α5 and pY397FAK, after tiarellic acid (TA) treatment.
Figure 15:
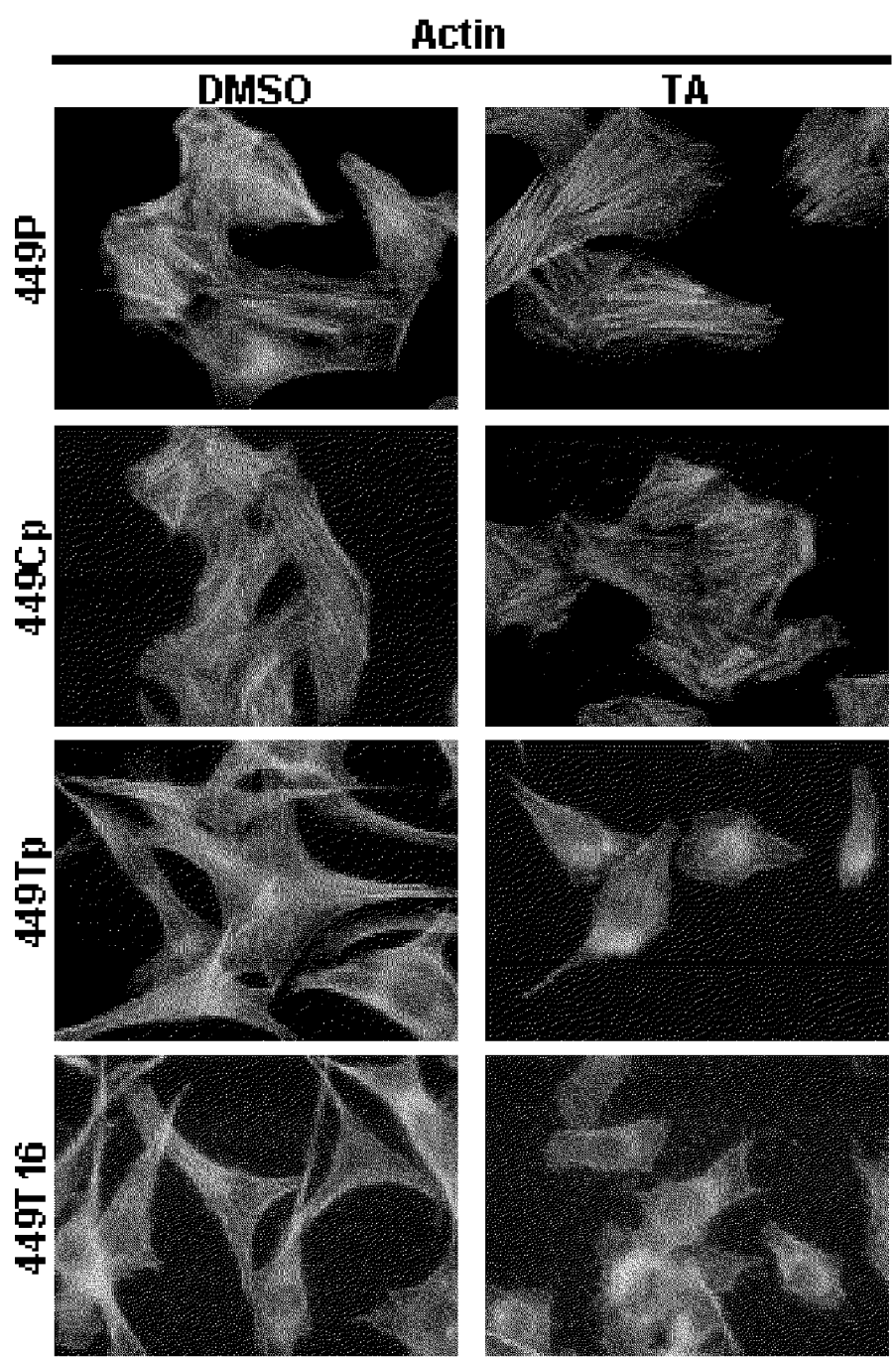
FIG. 15 shows loss of actin stress fiber formation, after tiarellic acid (TA) treatment.

Since tiarellic acid (TA) suppressed focal adhesion molecule activation and complex formation, focal adhesion formation would likely be affected by TA treatment. The present inventors thus analyzed focal adhesion formation in TA-treated and -untreated cells by performing immunostaining for Tyr397-phosphorylated FAK (pY$^{397}$FAK) or Tyr118-phosphorylated paxillin (pY$^{118}$paxillin). Although TA treatment did not affect focal adhesion formation in TM4SF5-null cells, focal adhesions in TM4SF5-expressing cells were lost after TA treatment. From the result of immunostaining for pY$^{397}$FAK or pY$^{118}$paxillin, disassembly of focal adhesion molecules was observed in TM4SF5-expressing cells (see FIG. 13). TA-mediated loss of focal adhesions appeared to involve a dissociation between integrin α5 and pY$^{397}$FAK in TM4SF5-expressing cells, being consistent with integrin mediated recruitment of focal adhesion molecules such as pY$^{397}$FAK (Lee, S. Y. et al., Focal adhesion and actin organization by a cross-talk of TM4SF5 with integrin α2 are regulated by serum treatment, Exp Cell Res, 312, pp. 2983-99, 2006) (see FIG. 14). Furthermore, since focal adhesions are linked to each other via stress fibers (Kaverina, I. et al., Regulation of substrate adhesion dynamics during cell motility, Int J BiochemCell Biol, 34, pp. 746-61, 2002), the present inventors also stained actin in TA-treated and -untreated cells. As shown in FIG. 15, it was found that TM4SF5-expressing cells showed abnormal actin organization with insignificant stress fibers after TA treatment, whereas TM4SF5-null cells did not (see FIG. 15). In TA-treated, TM4SF5-expressing cells, the loss of focal adhesions and actin stress fiber formation could contribute to the increase in the number of round shaped cells after TA treatment.

Experimental Example 3

Tiarellic Acid (TA)-Mediated Anoikis Induction in TM4SF5-Expressing Cells

TA treatment caused inactivation and disassembly of focal adhesion molecules, possibly contributing to a rounded morphology. Thus, it could be thought that TA treatment induces anoikis of TM4SF5-expressing cells. To examine whether TA treatment affected cellular adhesion, the following procedure was performed prior to analysis of TA-meditated cell death, as described in the literature (Yang, X. et al., Palmitoylation supports assembly and function of integrin-tetraspanin complexes, J Cell Biol, 167, pp. 1231-40, 2004).

Cells were treated with 20 μM TA for 24 hr, and the floating cells were collected and reseeded on fibronectin-precoated dishes for 1 hr before determination of the degree of adhesion.

Figure 16:
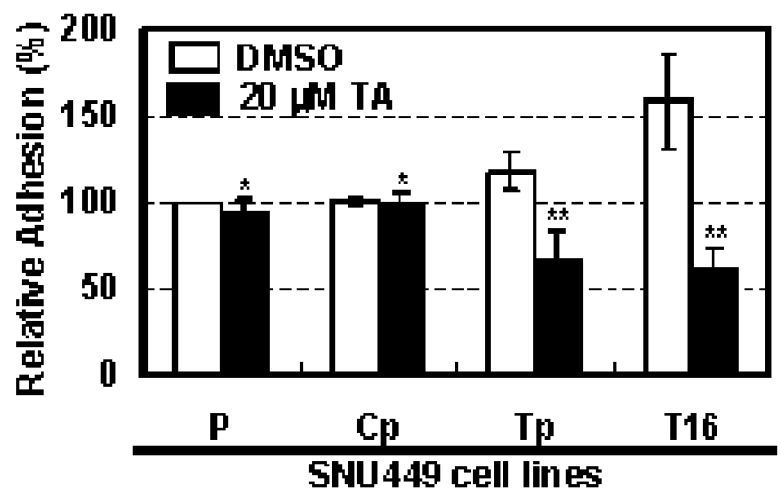
FIG. 16 is a graph showing the degree of adhesion in SNU449 cell lines, after tiarellic acid (TA) treatment.
Figure 17:
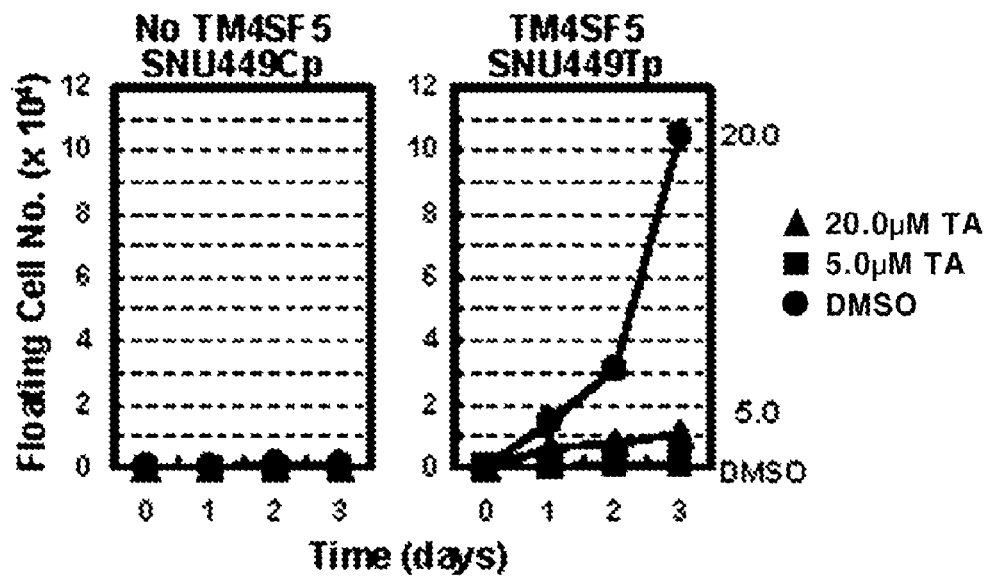
FIG. 17 is a graph showing the number of floating SNU449Cp and SNU449Tp cells, after tiarellic acid (TA) treatment for various time periods.
Figure 18:
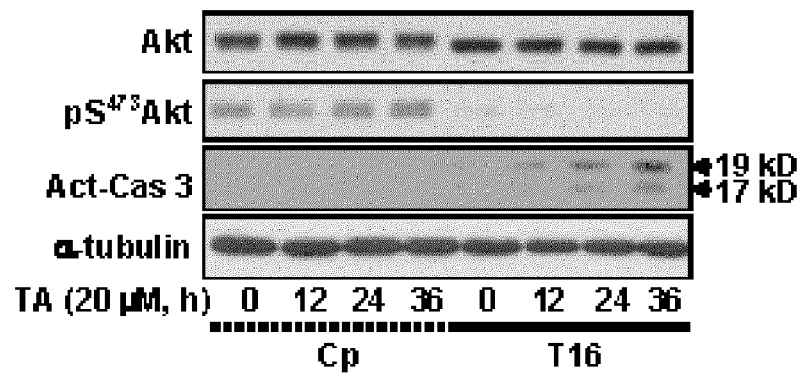
FIG. 18 is the result of Western blotting of cell survival and death-related signaling molecules, after tiarellic acid (TA) treatment for various time periods.
Figure 19:
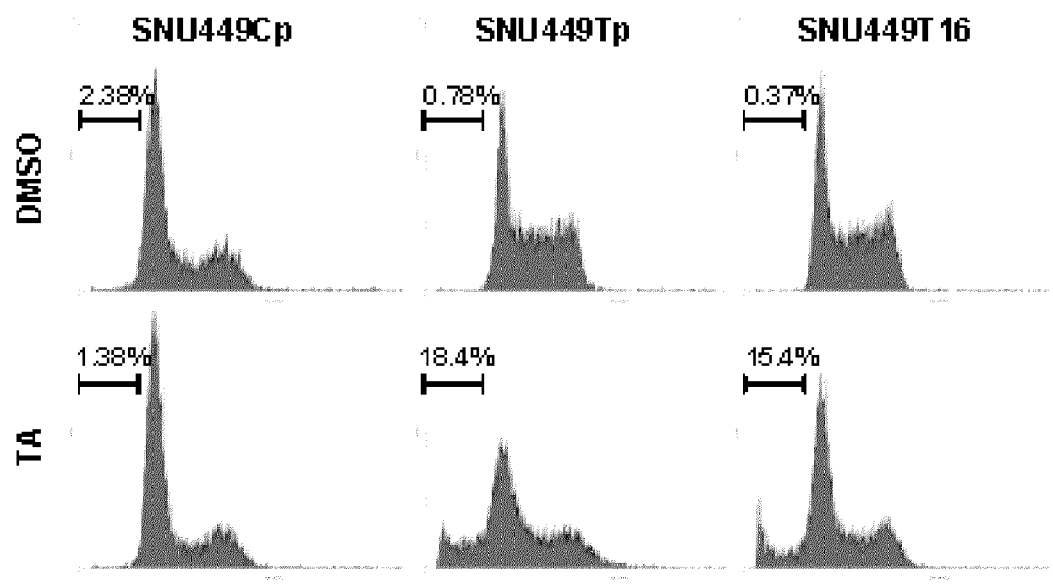
FIG. 19 is the result of analyzing cellular DNA content, after tiarellic acid (TA) treatment.

As shown in FIG. 16, adhesion of TM4SF5-null cells (SNU449P, SNU449Cp) was not affected by TA treatment, whereas TM4SF5-expressing cells (SNU449Tp, SNU449T16) pretreated with TA showed significantly reduced adhesions (see FIG. 16). Next, when floating cells were analyzed after TA or DMSO treatment, it was found that TA treatment increased the number of floating SNU449Tp cells expressing TM4SF5, but did not affect SNU449Cp cells expressing no TM4SF5 (see FIG. 17). In accordance with this result, TA treatment of TM4SF5-expressing SNU449T16 cells also resulted in Akt inactivation and caspase-3 activation (see FIG. 18). In addition, analysis of cellular DNA content after treatment with 20 μM TA for 24 hr resulted in significant sub-G1 populations of SNU449Tp and SNU449T16 expressing TM4SF5, but not of SNU449Cp cells expressing no TM4SF5 (see FIG. 19). Therefore, these observations suggest that TA causes anoikis in TM4SF5-expressing cells only.

Experimental Example 4

Tiarellic Acid (TA)-Mediated Effects on Overexpression of Focal Adhesion Molecules To evaluate whether overexpression of focal adhesion molecules such as focal adhesion kinase (FAK), paxillin, and p130Cas would block the effects of TA treatment, the following procedure was performed as described in the literature (Lee, S. Y. et al., Focal adhesion and actin organization by a cross-talk of TM4SF5 with integrin α2 are regulated by serum treatment, Exp Cell Res, 312, pp. 2983-99, 2006).

Figure 20:
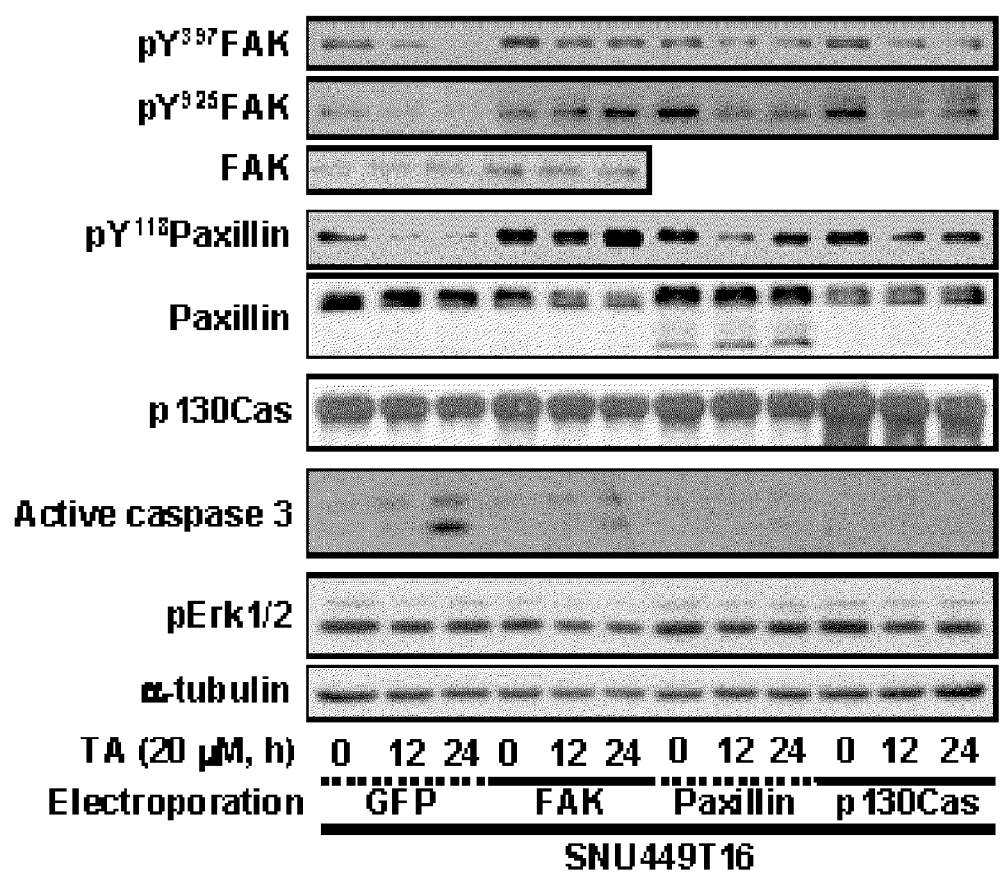
FIG. 20 shows the degrees of blocking TA-mediated effects by overexpression of wild type FAK, paxillin, or p130Cas in SNU449T16 cell.
Figure 21:
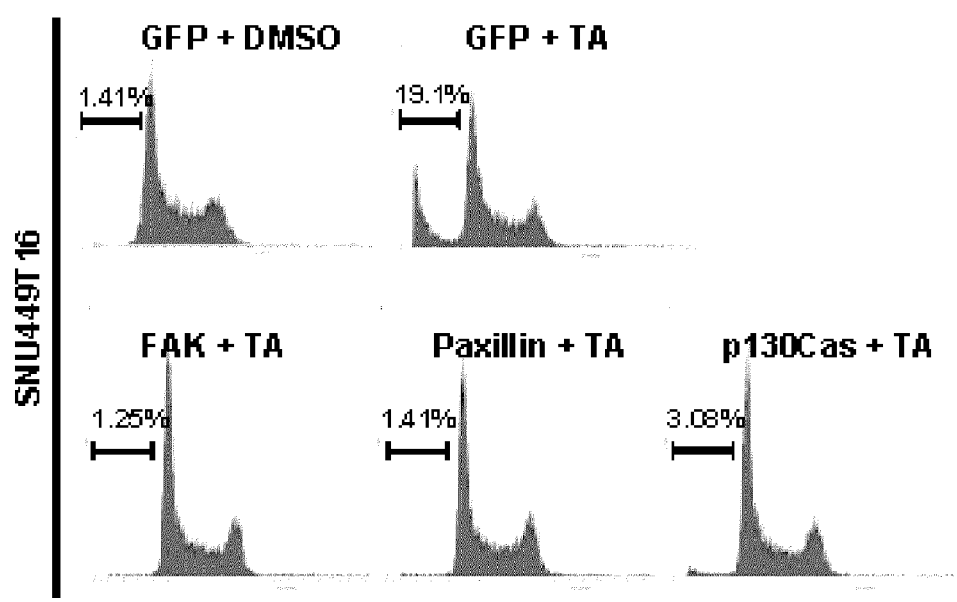
FIG. 21 is the result of analyzing DNA content, in which overexpression of focal adhesion molecules blocked tiarellic acid (TA)-mediated cell death.

To explore this, each cDNA was introduced into SNU449T16 cells via electroporation. After 1 day, the cells were treated with 20 μM TA for 24 hrs to obtain lysates. TA treatment of SNU449T16 cells introduced with control plasmid (for GFP) showed time-dependent inactivation of focal adhesion molecules and activation of caspase-3, supporting TA-mediated apoptosis. However, SNU449T16 cells introduced with wild-type focal adhesion kinase (FAK), paxillin, or p130Cas resulted in certain degrees of blocking TA-mediated effects (see FIG. 20). Furthermore, overexpression of the focal adhesion molecules also blocked TA-mediated increases in the sub-G1 population (see FIG. 21). Therefore, the TA-mediated effects on TM4SF5-expressing cells could be overcome to a certain degree by overexpression of focal adhesion molecules. On the other hand, changes in Erk1/2 activation were not observed under each experimental condition, thereby understanding TA-mediated effects on signal transduction in this experimental system.

Experimental Example 5

Effect of Tiarellic Acid (TA) on TM4SF5-Mediated Tumor Formation in Nude Mice

To evaluate whether tiarellic acid (TA) administration might interfere with TM4SF5 mediated tumor formation in nude mice, the following experiment was performed as described in the literature (Lee S-A et al., TM4SF5-mediated transmodulation between cytosolic p27Kip1 and Rho GTPases and epithelial-mesenchymal transition cause loss of contact inhibition, Cancer Cell, 2007).

Figure 22:
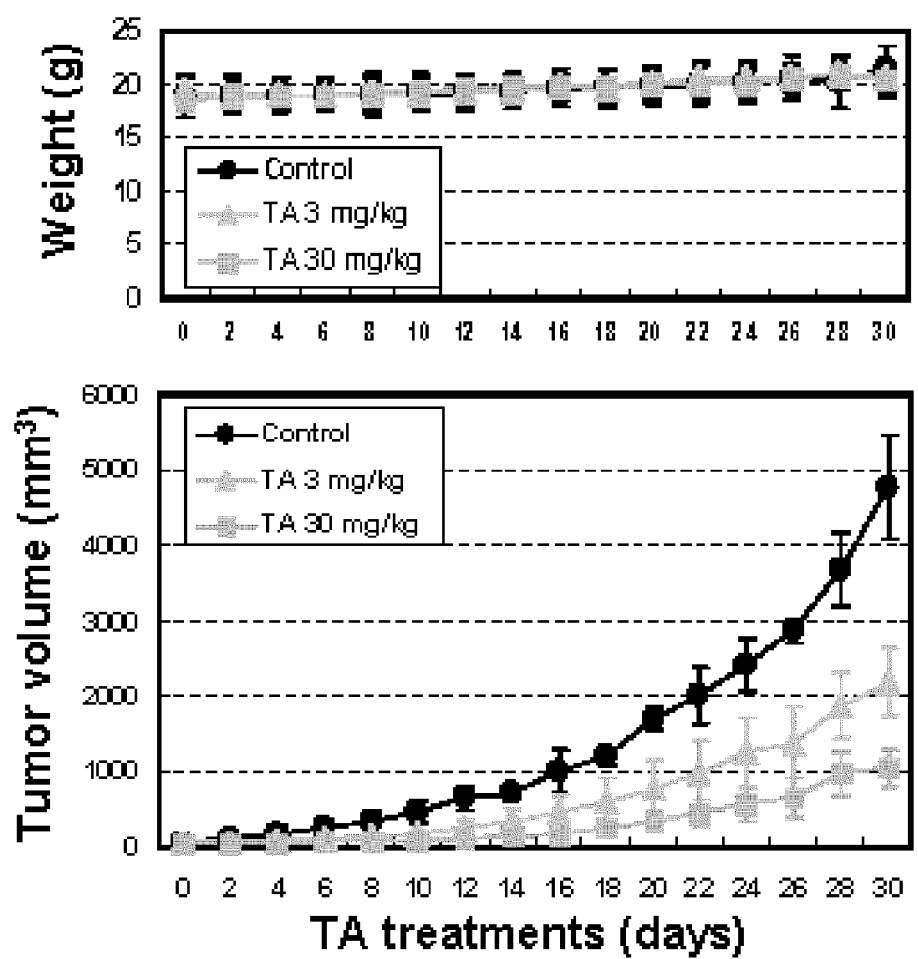
FIG. 22 shows changes in body weight and tumor volume of mouse injected with TM4SF5-expressing cell line, after tiarellic acid (TA) administration.
Figure 23:
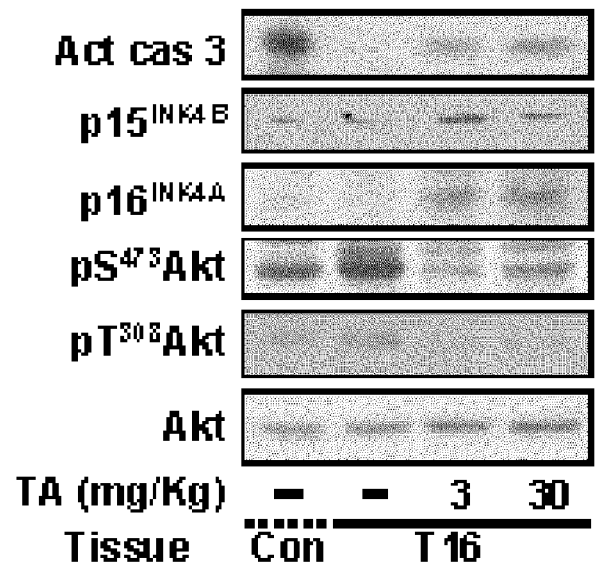
FIG. 23 shows induction of cell death in TM4SF5-mediated tumor tissue, after tiarellic acid (TA) administration.
Figure 24:
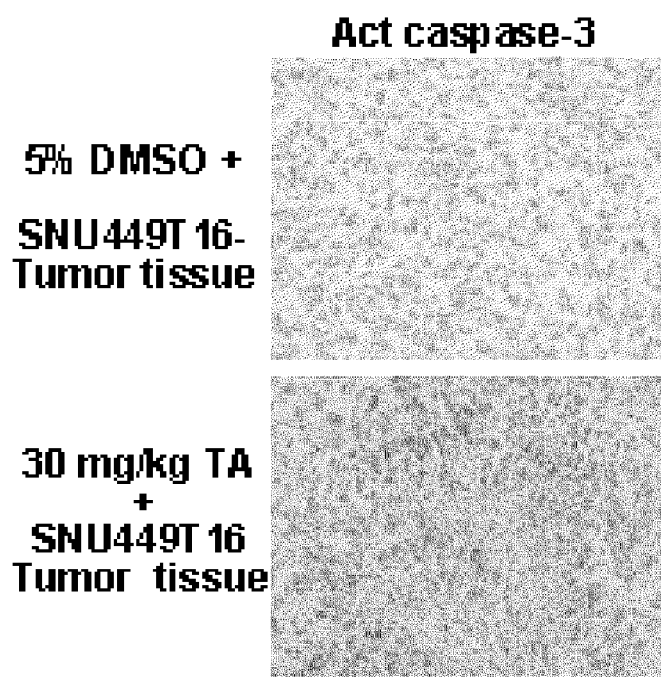
FIG. 24 shows caspase-3 activation in TM4SF5-mediated tumor tissue, after tiarellic acid (TA) administration.

As reported previously, nude mice injected with TM4SF5-expressing SNU449T16 cells formed significant tumors, whereas injection with TM4SF5-null SNU449Cp cells did not form tumors. When tiarellic acid (TA) was given intraperitoneally every other day for 30 days to mice with established tumors (~200 mm$^3$ of calculated tumor volume), TM4SF5-mediated tumor formation was decreased. As shown in FIG. 22, administration of tiarellic acid (TA) at 3 or 30 mg/kg body weight decreased the tumor volumes to 46.0% or 22.1%, respectively, while body weight increased normally, indicating no significant toxic side effects (see FIG. 22). Western blot analysis using control tissue around the spot injected with SNU449Cp cells and tumor tissue of SNU449Tp-injected mice revealed that TM4SF5-mediated tumor tissue showed Akt activation and caspase-3 inactivation, indicating signaling activities for tumor formation. However, TA administration decreased Akt activation, increased p15INK4B or p16INK4A CKI (cyclin-dependent kinase inhibitor) levels, and enhanced caspase-3 activation, indicating that TA caused growth inhibition and apoptosis in the TM4SF5-mediated tumors (see FIG. 23). Immunohistochemical staining for active caspase-3 was positive in TM4SF5-mediated tumor tissue obtained from mice that had been treated with TA (see FIG. 24). Therefore, TA specifically interfered with TM4SF5-mediated tumor formation in nude mice, presumably by enhancing apoptosis. These results suggest that TA might be developed further as a potential therapeutic reagent for TM4SF5-positive tumors.

Examples of pharmaceutical formulation comprising the extract or compound of the present invention will be described. However, these Examples are for illustrative purposes only, and the invention is not intended to be limited by these Examples.

Preparation Example 1

Preparation of Powder

| | |
|---|---|
| *Tiarella polyphylla* crude extract | 300 mg |
| Lactose | 100 mg |
| Talc | 10 mg |

The ingredients were mixed and filled in an airtight sac to prepare a powder agent.

Preparation Example 2

Preparation of Tablet

| | |
|---|---|
| Tiarellic acid | 50 mg |
| Corn Starch | 100 mg |
| Lactose | 100 mg |
| Magnesium Stearate | 2 mg |

A mixture of the ingredients was prepared into a tablet using a general tabletting method.

Preparation Example 3

Preparation of Capsule

| | |
|---|---|
| *Tiarella polyphylla* crude extract | 50 mg |
| Corn Starch | 100 mg |
| Lactose | 100 mg |
| Magnesium Stearate | 2 mg |

A mixture of the ingredients was filled into a gelatin capsule according to a typical procedure, so as to give a capsule agent.

Preparation Example 4

Preparation of Injectable Formulation

| | |
|---|---|
| Tiarellic acid | 50 mg |
| Sterile distilled water | proper amount |
| pH adjuster | proper amount |

According to a typical procedure, an injectable formulation comprising the above ingredients was prepared into a (2 ml) ampule.

Preparation Example 5

Preparation of Liquid Formulation

| | |
|---|---|
| *Tiarella polyphylla* crude extract | 100 mg |
| High fructose corn syrup | 10 g |
| Mannitol | 5 g |
| Purified water | proper amount |

According to a typical procedure, each ingredient was solubilized in purified water. A proper amount of lemon flavor was added to the above ingredients, and mixed. Then, purified water was added to a volume of 100 ml, filled in a brown bottle, and sterilized to prepare a liquid formulation.

Preparation Example 6

Preparation of Health Food

| | |
|---|---|
| Tiarellic acid | 1000 mg |
| Vitamin mixture | proper amount |
| Vitamin A acetate | 70 µg |
| Vitamin E | 1.0 mg |
| Vitamin | 0.13 mg |
| Vitamin B2 | 0.15 mg |
| Vitamin B6 | 0.5 mg |
| Vitamin B12 | 0.2 µg |
| Vitamin C | 10 mg |
| Biotin | 10 µg |
| Nicotinic acid amide | 1.7 mg |
| Folic acid | 50 µg |
| Calcium pantothenate | 0.5 mg |
| Mineral mixture | proper amount |
| Ferrous sulfate | 1.75 mg |
| Zinc oxide | 0.82 mg |
| Magnesium carbonate | 25.3 mg |
| Potassium dihydrogen phosphate | 15 mg |
| Potassium monohydrogen phosphate | 55 mg |
| Potassium citrate | 90 mg |
| Calcium carbonate | 100 mg |
| Magnesium chloride | 24.8 mg |

The composition of vitamin and mineral mixtures followed the preferable combination of each suitable ingredient, but can be optionally modified. The above ingredients were mixed according to the conventional health food production method to prepare granules for further use as a health food composition.

Preparation Example 7

Preparation of Health Beverage

| | |
|---|---|
| *Tiarella polyphylla* crude extract | 1000 mg |
| Citric acid | 1000 mg |
| Oligosaccharides | 100 g |
| Plum concentrate | 2 g |
| Taurine | 1 g |
| Purified water | filled to 900 ml |

The above ingredients were mixed according to the conventional health beverage production method, and the mixture was heated with stirring at 85° C. for one hour. The solution was filtered and stored in a sterilized 2 L container with sealed and sterilized. The container was then stored in a refrigerator for further use as a health beverage composition.

The beverage composition followed the preferable combination of each component, but not always limited thereto, and can be modified considering demand class, demand country, purpose of use, local and national preference, etc.

INDUSTRIAL APPLICABILITY

A *Tiarella polyphylla* extract, a tiarellic acid compound isolated therefrom or a pharmaceutically acceptable salt thereof of the present invention exhibits the effects of reducing cancer cell proliferation and inducing cell death, thereby being used as a pharmaceutical composition for preventing and treating cancer diseases and a functional health food.

noma of papilla vateri, soft tissue sarcoma, nonendocrine lung cancer, ACTH (corticotropin)-negative bronchial carcinoid tumor and liver cancer, and wherein the cancer cell-specific anoikis-inducing agent comprises tiarellic acid, or a pharmaceutically acceptable salt thereof or a *Tiarella polyphylla* extract comprising the same.

2. The method according to claim 1, wherein the extract is a crude extract or an extract soluble in a polar solvent.

3. The method according to claim 2, wherein the crude extract is an extract being soluble in solvent, wherein said solvent comprises purified water, C1-C4 lower alcohol, or the mixtures thereof.

4. The method according to claim 2, wherein the extract soluble in a polar solvent is an extract being soluble in a solvent selected from the group consisting of water, methanol, ethanol, butanol, and the mixtures thereof.

5. The method according to claim 1, wherein the tiarellic acid, pharmaceutically acceptable salt thereof or *Tiarella polyphylla* extract comprising the same is administered in the form of a dietary supplement composition.

6. The method according to claim 5, wherein the dietary supplement composition is in the form of a tablet, a capsule, a pill, or liquid.

The invention claimed is:

1. A method of treating cancer, comprising:
administrating to a patient in need thereof a cancer cell-specific anoikis-inducing agent, thereby treating cancer, wherein the cancer being treated is TM4SF5 expressing cancer which is selected from the group consisting of pancreatic cancer, gastric cancer, colon cancer, carci-

* * * * *

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: forward primer

<400> SEQUENCE: 1
atgtgtacgg gaaaatgtgc ccgct                               25

<210> SEQ ID NO 2
<211> LENGTH: 23
<212> TYPE: DNA
<213> ORGANISM: Artificial Sequence
<220> FEATURE:
<223> OTHER INFORMATION: reverse primer

<400> SEQUENCE: 2
agtgaggtgt gtcctgtttt ttc                                 23